United States Patent
Misholi

(10) Patent No.: US 7,527,054 B2
(45) Date of Patent: May 5, 2009

(54) APPARATUS AND METHOD FOR CONTROLLING FRACTION OF INSPIRED OXYGEN

(75) Inventor: Boaz Misholi, New York, NY (US)

(73) Assignee: General Electric Company, Schenectady, NY (US)

( * ) Notice: Subject to any disclaimer, the term of this patent is extended or adjusted under 35 U.S.C. 154(b) by 757 days.

(21) Appl. No.: 11/136,087

(22) Filed: May 24, 2005

(65) Prior Publication Data

US 2006/0266355 A1   Nov. 30, 2006

(51) Int. Cl.
  A62B 7/00   (2006.01)
  A61M 16/00  (2006.01)

(52) U.S. Cl. .......................... 128/204.22; 128/205.11; 128/204.23; 128/204.21; 128/204.18

(58) Field of Classification Search ............ 128/200.24, 128/203.12, 203.13, 203.14, 203.16, 203.17, 128/204.18, 204.21, 204.23, 204.22, 205.11, 128/203.25, 203.26, 203.27
See application file for complete search history.

(56) References Cited

U.S. PATENT DOCUMENTS

| | | | |
|---|---|---|---|
| 4,889,116 A | 12/1989 | Taube | |
| 5,103,814 A | 4/1992 | Maher | |
| 6,186,142 B1 | 2/2001 | Schmidt et al. | |
| 6,192,883 B1 | 2/2001 | Miller, Jr. | |
| 6,584,973 B1 | 7/2003 | Biondi et al. | |
| 6,761,165 B2 | 7/2004 | Strickland, Jr. | |
| 6,786,217 B2 | 9/2004 | Stenzler | |
| 6,789,539 B2 | 9/2004 | Martinez | |
| 6,796,305 B1 | 9/2004 | Banner et al. | |
| 6,796,306 B2 | 9/2004 | Martinez | |
| 6,810,876 B2 | 11/2004 | Berthon-Jones | |
| 6,814,076 B2 | 11/2004 | Shusterman et al. | |
| 6,823,866 B2 | 11/2004 | Jafari et al. | |
| 6,840,240 B1 | 1/2005 | Berthon-Jones et al. | |
| 6,845,773 B2 | 1/2005 | Berthon-Jones et al. | |
| 6,849,049 B2 | 2/2005 | Starr et al. | |
| 6,851,426 B1 | 2/2005 | Stromberg | |
| 6,854,462 B2 | 2/2005 | Berthon-Jones et al. | |
| 6,866,040 B1 | 3/2005 | Bourdon | |
| 6,868,346 B2 | 3/2005 | Larson et al. | |
| 7,201,734 B2 * | 4/2007 | Hickle .......................... | 604/67 |
| 7,247,154 B2 * | 7/2007 | Hickle .......................... | 604/500 |
| 2001/0039951 A1 | 11/2001 | Strickland | |
| 2002/0072659 A1 | 6/2002 | Claure et al. | |

FOREIGN PATENT DOCUMENTS

EP   0504725   9/1992

* cited by examiner

*Primary Examiner*—Justine R Yu
*Assistant Examiner*—Annette F Dixon

(57) ABSTRACT

A method and apparatus for operating a ventilator to control the fraction of pressure inspired oxygen ($FiO_2$) to a patient that includes: providing a ventilator controller that includes a software algorithm, apulse oximeter and a $FiO_2$ flow rate controller; measuring the pulse oximetry of the patient and computing an average pulse oximetry value over a time period; selecting a first, second and third pulse oximetry levels as set points for the ventilator controller; selecting an update time interval; decreasing the $FiO_2$ flow rate by a first incremental amount when the average pulse oximetry value is greater than the first level; increasing the $FiO_2$ flow rate by a second incremental amount when the average pulse oximetry value is less than the second level; increasing the $FiO_2$ flow rate to the maximum and initiating an alarm condition when the average pulse oximetry value is less than the third level.

24 Claims, 2 Drawing Sheets

APPARATUS AND METHOD FOR CONTROLLING FRACTION OF INSPIRED OXYGEN

FIELD OF THE INVENTION

This invention relates to a method and apparatus for controlling a ventilator which allows a doctor to prescribe the amount of oxygen delivered to a patient. Particularly, the invention concerns a method and apparatus for automatically controlling the fraction of inspired oxygen ($FiO_2$) supplied to a patient.

BACKGROUND OF INVENTION

Ventilation using mechanical ventilators is widely accepted as an effective form of therapy and means for treating patients who require respiratory assistance. Ventilation is the process of delivering oxygen to and washing carbon dioxide from the alveoli in the lungs. A medical ventilator delivers gas to a patient's respiratory tract and is often required when the patient is unable to maintain adequate ventilation. Mechanical ventilation is the single most important therapeutic modality in the care of critically ill patients. Known ventilators typically include a pneumatic system with variable pressure, flow and volume characteristics that delivers and extracts air and/or gas to the patient and a control system (typically consisting of a microprocessor with a keypad and a display) that provides the interface to the treating clinician. Optimal support of the patient's breathing requires adjustment by the clinician of the pressure, flow, and volume of the delivered gas as the condition of the patient changes. Such adjustments, although highly desirable, are difficult to implement with known ventilators because the control system demands continuous attention and interaction from the clinician based on the patient's condition.

Medical ventilator systems have been used for many years to provide supplemental oxygen support to patients unable to breathe normally. These medical ventilators typically include a source of pressurized oxygen, a flow generator, an air filter, a mask, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors typically measure motor speed, gas volumetric flow rate and outlet pressure. The apparatus may optionally include a humidifier in the air delivery circuit. The controller may also include data storage capacity with or without integrated data retrieval and display functions.

Most modern ventilators allow the clinician to select and use several modes of inhalation either individually or in combination via the ventilator setting controls that are common to the ventilators. These modes can be defined in three broad categories: spontaneous, assisted or controlled. During spontaneous ventilation without other modes of ventilation, the patient breathes at his own pace, but other interventions may affect other parameters of ventilation including the tidal volume and the baseline pressure (above ambient) within the system. In assisted ventilation, the patient initiates the inhalation by lowering the baseline pressure by varying degrees, and then the ventilator "assists" the patient by completing the breath by the application of positive pressure. During controlled ventilation, the patient is unable to breathe spontaneously or initiate a breath, and is, therefore, dependent on the ventilator for every breath. During spontaneous or assisted ventilation, the patient is required to "work" (to varying degrees) by using the respiratory muscles in order to breath.

The simplest way to look at mechanical ventilation is as a way to keep the blood gases normal. The most relevant parameters of a normal blood gas are hydrogen ion concentration (pH), partial pressure of carbon dioxide ($pCO_2$) and partial pressure of oxygen ($pO_2$). There are several other values, but many of these are calculated and/or not reflective of pulmonary function which is what is being controlled with mechanical ventilation. Hydrogen ion concentration and partial pressure of carbon dioxide are closely related and are affected by minute ventilation (respiratory rate times tidal volume or RR×TV). Partial pressure of oxygen is governed by oxygen delivery and ventilation and perfusion (V and Q) match. Because $CO_2$ rapidly diffuses across the alveolar space, the more air that is moved into and out of the lungs, the more rapidly the $CO_2$ can be removed.

Oxygen delivery is dependent on ventilation and perfusion match and partially determined by a patient's fraction of inspired oxygen ($FiO_2$) and is partly related to the patient's airway recruitment. Airway recruitment is indirectly reflected in the patient's mean airway pressure (MAP). By increasing the patient's mean airway pressure, airway recruitment can be increased (although this is not a linear relationship). Mean airway pressure is a function of the positive end expiratory pressure (PEEP) and a fraction of the peak inspiratory pressure (PIP or Pmax).

Oxygen therapy or the supplemental oxygen treatment of patients on mechanical ventilation is crucial in maintaining the patients' oxygen levels in the normal range. Oxygen therapy is defined as the administration of oxygen at concentrations greater than ambient air (approximately 21% oxygen). The percentage of oxygen in the air inhaled by a patient, either on or off the ventilator, is called the fraction of inspired oxygen ($FiO_2$). $FiO_2$ ranges are from 21% (e.g. ambient room air) to 100% (e.g. pure oxygen). Typically, an $FiO_2$ not exceeding 0.25-0.35 is needed and a 0.05 variation in $FiO_2$ is generally clinically acceptable. For most patients, a precise or high inspiratory oxygen fraction ($FiO_2$) is not required. In some ventilators, $FiO_2$ is increased by the attachment of an oxygen ($O_2$) accumulator to the gas entry port. Alternatively, supplemental $O_2$ may be titrated into the inspiratory limb of the ventilator circuit between the ventilator and the humidifier or, during noninvasive positive pressure ventilation (NPPV), via oxygen tubing connected directly to the mask.

Monitoring the arterial oxygen saturation ($SpO_2$) using pulse oximetry is a simple non-invasive method (i.e., the skin does not have to be broken to perform the test), which allows health care providers to monitor the oxygen-bound hemoglobin of a patient's blood. Pulse oximetry measures the ratio of oxygenated hemoglobin to the total amount of hemoglobin, i.e., the percentage of haemoglobin (Hb) which is saturated with oxygen, or the amount of oxygen in the blood of the arteries. The pulse oximeter uses two wavelengths of light (650 nm (red) and 805 nm (infrared)) originating from a probe and passing through the patient's skin (preferably the patient's finger, ear lobe or toe). The light is partly absorbed by haemoglobin, by amounts which differ depending on whether the haemoglobin is saturated or desaturated with oxygen. A sensor measures the amount of light the tissue absorbs and the output from the sensor is linked to a microprocessor. By calculating the light absorption at the two wavelengths, the microprocessor can compute the proportion of haemoglobin which is oxygenated.

Based upon the ratio of absorption of the red and infrared light caused by the difference in color between oxygen-bound (red) and unbound (blue) hemoglobin in the capillary bed, an approximation of oxygenation can be made. The pulse oximeter displays the percentage of Hb saturated with oxygen together with an audible signal for each pulse beat, a calculated heart rate and in some models, a graphical display of the blood flow past the probe (plethysmograph). The pulse oximeter provides a means to determine how well the patient is being oxygenated. The oximeter is dependant on a pulsatile flow and produces a graph of the quality of flow. Where flow is sluggish (e.g., hypovolaemia or vasoconstriction), the pulse oximeter may be unable to function. The computer within the oximeter is capable of distinguishing pulsatile flow from other more static signals (such as tissue or venous signals) to display only the arterial flow.

The previously known medical ventilators generally require a user interface to successfully adjust and maintain the patient's $FiO_2$. This is most likely due to the complex and non-linear behavior of the human body's response to various physiological stimuli. Accordingly, there is a need for a ventilator system that can effectively automatically control the fraction of inspired oxygen based on the patient's $SpO_2$.

SUMMARY OF THE INVENTION

In accordance with the present invention, a ventilator system and a method of operating a ventilator to control the fraction of pressure inspired oxygen ($FiO_2$) to a patient is provided. The method includes: providing a pulse oximeter to measure a patient's pulse oximetry ($SpO_2$), a ventilator controller responsive to an average of the patient's measured pulse oximetry value and a $FiO_2$ flow rate controller responsive to the ventilator controller, wherein the flow rate controller controls the flow rate of $FiO_2$ to the patient. The method also includes: measuring the pulse oximetry of the patient and providing a measured pulse oximetry value; averaging the patient's measured pulse oximetry value over a period of time; selecting the time period for averaging the patient's measured pulse oximetry value; selecting an $FiO_2$ operating range having a low end, a high end and a mid-point, wherein the midpoint of the range is equal to one-half the sum of the low end and the high end; selecting a first incremental amount for decreasing the flow rate of $FiO_2$ and a second incremental amount for increasing the flow rate of $FiO_2$; setting the $FiO_2$ flow rate controller at a flow rate equal to the mid-point of the range; selecting a first, a second, and a third pulse oximetry level as set points for the ventilator controller; selecting an update time interval, wherein the update time interval is the interval of time between comparisons by the ventilator controller of the set points and the measured pulse oximetry of the patient; decreasing the flow rate of $FiO_2$ by the first incremental amount when the pulse oximetry is greater than the first level and the flow rate is greater than or equal to the low end of the $FiO_2$ operating range; increasing the flow rate of $FiO_2$ by the second incremental amount when the pulse oximetry is less than the second level and the flow rate is less than or equal to the high end of the $FiO_2$ operating range; and increasing the flow rate of $FiO_2$ to a maximum rate, preferably 100%, when the pulse oximetry is less than the third level and initiating an alarm condition.

The ventilator controller includes software which automatically adjusts the flow rate of $FiO_2$ based upon the average pulse oximetry value of the patient. The ventilator controller can also include a normal operating mode for the control of the flow rate of $FiO_2$, wherein the flow rate of $FiO_2$ is automatically controlled between the first and second pulse oximetry level set points and the flow rate does not change when the pulse oximetry is between the first level and the second level. The an $FiO_2$ operating range is between about 40% and 100%, and preferably between 60% and 90%. The update time interval is at least 10 seconds, preferably at least 30 seconds. The period of time over which the measured pulse oximetry value is averaged is between 5 and 60 seconds before the end of the update time interval, preferably over the last 10 seconds. In addition, the alarm condition can actuate an audible alarm signal, a visual alarm signal or both an audible alarm signal and a visual alarm signal. The alarms must be acknowledged and manually reset by the operator. In preferred embodiments, the pulse oximetry is measured using a probe attached to the patient's finger, toe or ear lobe.

The present invention also includes a ventilator system for controlling the fraction of pressure inspired oxygen ($FiO_2$) in air delivered to a patient. The ventilator system includes: a pulse oximeter which measures the pulse oximetry of a patient and generates an output signal in response thereto; a ventilator controller comprising a keypad, a display and a software algorithm, wherein the keypad and display are adapted to enter an update time interval, a first, second, and third pulse oximetry level set points, a $FiO_2$ flow rate range, a first incremental amount for decreasing the flow rate of $FiO_2$ and a second incremental amount for increasing the flow rate of $FiO_2$; and a time period over which the patient's measured pulse oximetry value is averaged; a $FiO_2$ flow rate controller, which preferably includes a control valve, responsive to the ventilator controller; and a face mask, nasal mask or endotracheal tube for delivering the air to the patient.

The ventilator controller software algorithm compares the patient's averaged pulse oximetry value to the first, second and third pulse oximeter level set points. Based on the average pulse oximeter level, the ventilator controller automatically controls the flow rate of $FiO_2$ to the patient such that the flow rate of $FiO_2$ decreases by the first incremental amount when the pulse oximetry is greater than the first level, increases the flow rate of $FiO_2$ by the second incremental amount when the pulse oximetry is less than the second level, and increases the flow rate of $FiO_2$ to a maximum rate when the pulse oximetry is less than the third level. The update time interval is the interval of time between comparisons by the ventilator controller software algorithm of the set points and the average pulse oximetry value.

BRIEF DESCRIPTION OF THE FIGURES

Other objects and attendant features of this invention will be readily appreciated as the invention becomes better understood by reference to the following detailed description when considered in connection with the accompanying drawings wherein.

DETAILED DESCRIPTION OF THE INVENTION

Figure 1:
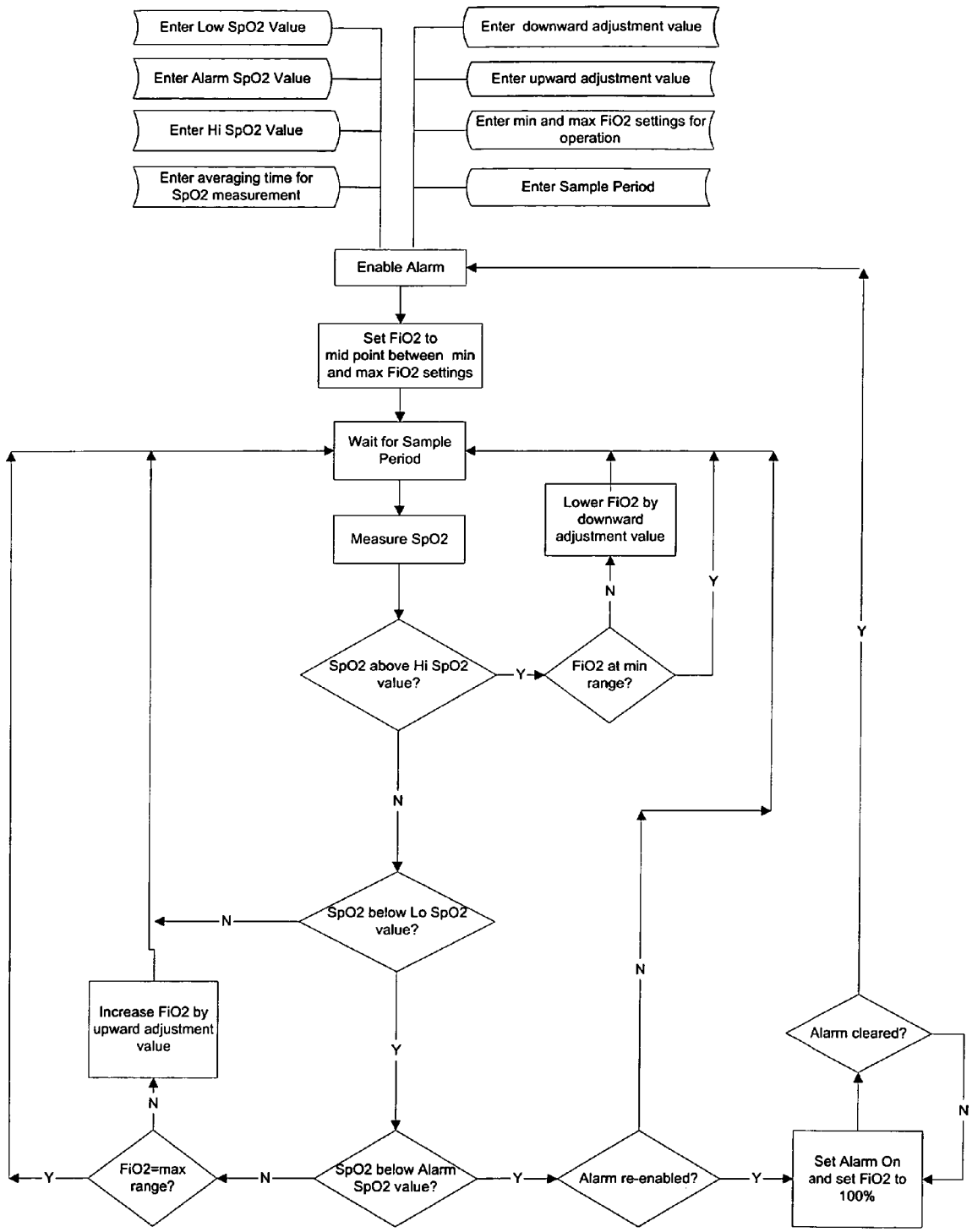
FIG. 1 is a flow chart showing the operation of an embodiment of the ventilator control algorithm.

The present invention provides both a ventilator system and a method for controlling a ventilator, which allows a doctor to prescribe how oxygen is to be delivered to a patient. The ventilator system includes a pulse oximeter which measures the arterial oxygen saturation ($SpO_2$) of a patient using a ventilator. The output signal is sent to a ventilator controller which calculates an average value of the measured pulse oximetry, regulates the air to the patient and controls the $FiO_2$ flow rate. The ventilator controller is programmed with a software algorithm and has a display and a keypad for monitoring and controlling the ventilation of the patient. To initialize the ventilator controller, a technician enters pulse oximetry set point levels, the values for the incremental changes in the $FiO_2$ flow rate, the update time, the initial $FiO_2$ range and other pertinent data relating to the patient. The ventilator controller compares the average measured pulse oximeter value to the set point levels entered by the technician and regulates the $FiO_2$ flow rate.

The method uses a pulse oxygen saturation ($SpO_2$) monitor, a ventilator controller, $FiO_2$ flow rate controller and software including an algorithm for controlling the fraction of inspired oxygen ($FiO_2$) delivered to the patient. In operation, the doctor can program the ventilator controller so that the system delivers a predetermined amount of $FiO_2$ to the patient in response to changes in the $SpO_2$. Programming the ventilator controller includes selecting the settings for certain decision points. These decision points are based on the patient's $SpO_2$ level and control the raising or lowering of the $FiO_2$ flow rate. The doctor is also able to select the magnitude of response at each of these decision points. The initial programming of the ventilator controller also includes the selection of an operating range for the $FiO_2$ flow rate, preferably from 40-100% and most preferably from 60-90% of the range of the flow controller. The initial $FiO_2$ flow rate setting is equal to the mid-point of the selected operating range, i.e., one half of the sum of the lower end of the range plus the upper end of the range. For example, when a 60-90% $FiO_2$ flow rate range is selected, the initial set point is 75% (the mid-point of the range).

The method of the present invention can use a variety of different ventilator systems that are well known in the art. Examples of the different ventilator systems that can be used are disclosed in U.S. Pat. No. 6,186,142 to Schmidt et al.; U.S. Pat. No. 6,584,973 to Biondi et al.; U.S. Pat. No. 6,796,305 to Banner et al.; U.S. Pat. No. 6,810,876 to Berthon-Jones; and U.S. Pat. No. 6,845,773 to Berthon-Jones, all of which are incorporated herein by reference in their entirety.

The patient's $SpO_2$ is measured as an average of the $SpO_2$ output signal over a predetermined interval of time. The patient's $SpO_2$ can vary with each heartbeat and, therefore, an average value is more indicative of the patient's condition at any point in time. Accordingly, an average $SpO_2$ value is calculated over an interval immediately prior to the expiration of the "update time" interval. The $SpO_2$ output signal is averaged over an interval of from 5 to 60 seconds prior to the expiration of the "update time" interval. Preferably, the $SpO_2$ output signal is averaged over the last 10 seconds prior to the expiration of the "update time" interval.

The preferred ventilator systems that are used for the present invention include a variably actuatable valve that is connected in series with the fluid conduit to vary the fraction of positive pressure inspired oxygen ($FiO_2$) to the patient. $FiO_2$ can vary between 0.21 (the oxygen concentration in ambient air), in which no supplemental oxygen support is provided to the patient, and 1.0, in which pure oxygen is provided to the patient. In order to determine the proper $FiO_2$, the arterial oxygen saturation ($SpO_2$) is monitored by the pulse oximeter attached to the patient. The $SpO_2$ is ideally in the range of 0.97-1.0 whereas an $SpO_2$ of less than 0.91 is dangerously low. The ventilator controller averages the measured pulse oximetry of the patient over a predetermined period of time, typically the last 5 to 60 seconds before the end of a predetermined update time interval, preferably over the last 10 seconds. The software algorithm changes the flow rate of $FiO_2$ when the average measured pulse oximetry value is above or below predetermined $SpO_2$ decision point levels. For example, the $FiO_2$ is increased when the $SpO_2$ decreases below a predetermined level.

The software algorithm allows the technician operating the ventilator to program the controller to initiate action at three "decision points" and change the flow rate of $FiO_2$ to the patient based on the patient's average measured $SpO_2$ value. The three decision points are referred to as the "step-up" decision point, the "step-down" decision point and the "alarm" decision point. The decision points are selected by the doctor and programmed into the controller by the technician operating the ventilator.

The controller continuously monitors the patient's $SpO_2$ but only changes the flow rate of $FiO_2$ to the patient at predetermined intervals. The predetermined interval is referred to as the "update time" and it is entered by the technician in accordance with the doctor's instructions. The "update time" can vary from about 10 seconds to about 30 minutes with the most preferred ranges having a lower value of at least 30 seconds and an upper value of less than 5 minutes. At the "update time," the controller compares the patient's averaged measured $SpO_2$ value with the three decision points and initiates, if required, changes the flow rate of $FiO_2$ to the patient based on the algorithm. The $FiO_2$ operating range is selected by the physician and initially programmed into the controller by the technician prior to the first use of the ventilator system. The $FiO_2$ flow rate is initially set at a rate equal to the mid-point of the operating range. After the $FiO_2$ flow rate has been adjusted, it remains at that rate until changed, either automatically when a decision point is reached or when it is manually changed by the technician.

The "step-up" decision point is a low $SpO_2$ level. If the output signal from the pulse oximeter is equal to or less than the "step-up" decision point at the "update time," the controller sends a signal to the ventilator to increase the flow rate of $FiO_2$ to the patient. The amount that the $FiO_2$ increases when the "step-up" decision point initiates action by the controller is an incremental value of between about 2 and about 10% and is called the "step-up value." The step-up value is selected by the doctor during the initial set-up and entered by the operator when the "step-up" decision point is entered. If the output signal from the pulse oximeter is still equal to or less than the "step-up" decision point at the subsequent "update time," the controller once more increases the flow rate of $FiO_2$ to the patient by the "step-up value." This continues until the $SpO_2$ level is above the "step-up" decision point, or until the $FiO_2$ reaches the upper operating range of the $FiO_2$ (entered during setup).

The "step-down" decision point is a high $SpO_2$ level. If the output signal from the pulse oximeter is equal to or greater than the "step-down" decision point at the "update time," the controller sends a signal to the ventilator to decrease the flow rate of $FiO_2$ to the patient. The amount that the $FiO_2$ decreases upon the "step-down" decision point is a value between about 2 and about 10% and is also entered by the clinician. The step-down value is selected by the doctor and entered during the initial set-up by the operator when the "step-down" decision point is entered. If the output signal from the pulse oximeter is still equal to or greater than the "step-down" decision point at the subsequent "update time," the controller once more decreases the flow rate of $FiO_2$ to the patient by the "step-down value." This continues until the $SpO_2$ level is below the "step-down" decision point, or the $FiO_2$ reaches the lower operating range of the $FiO_2$ setting.

The "alarm" decision point is a low limit of $SpO_2$ that is set below the "step-up" decision point. When the "alarm" decision point is reached, the controller initiates an automatic rescue mode (also referred to herein as an "alarm condition"). The automatic rescue mode signals the ventilator to increase the flow rate of $FiO_2$ to the maximum (100%) and sounds audio and/or visual alarms.

The software algorithm that is used to control the flow rate of $FiO_2$ to the patient has several advantageous features. First, the software algorithm does not continuously adjust oxygen in response to the patient's $SpO_2$. This allows the patient's body to respond to the change in $FiO_2$ flow rate before further changes are made. Second, the algorithm provides a safety mechanism to prevent hypoxia, i.e., the diminished amount (reduced saturation) of oxygen in arterial blood. By detecting a low $SpO_2$ condition and taking remedial steps to gradually increase the $FiO_2$ flow rate, the algorithm does not allow the patient's $SpO_2$ to reach critical levels. Third, the algorithm automatically initiates the steps that a doctor would prescribe for an abnormal $SpO_2$ level without a health care provider being present. Thus, the ventilator system controlled by the software algorithm has the advantage of operating at all times according to the physician's instructions.

Referring to FIG. 1, a preferred embodiment of the present invention is shown, wherein the ventilator controller is initialized by entering: the three decision points (low $SpO_2$, high $SpO_2$ and alarm $SpO_2$); the downward $FiO_2$ flow rate adjustment value; the upward $FiO_2$ flow rate adjustment value; the update time interval; the interval over which the $SpO_2$ value is averaged; and the $FiO_2$ flow rate range. The ventilator controller then automatically sets the initial $FiO_2$ flow rate at the midpoint of the $FiO_2$ flow rate range.

When the update time interval times out, the software algorithm compares an average of the pulse oximeter output signal ($SpO_2$) over a predetermined interval to the pre-selected decision points. If the alarm condition has not been initiated, the controller is maintained in a "normal operating mode." In the normal operating mode, the controller automatically controls the operation of the ventilator and the maintains the amount of $FiO_2$ in the air that patient is breathing at a constant level. The attending doctor can vary the operation of the controller by changing the update time, the time interval over which the average $SpO_2$ is measured, the settings for the decision points, the operating $FiO_2$ range or the increments by which the $FiO_2$ flow rate is adjusted.

The software algorithm monitors the pulse oximeter output signal for a high $SpO_2$ condition. If a high $SpO_2$ condition is detected (i.e., the "step-down" decision point), the controller sends a signal to decrease the $FiO_2$ flow rate by a pre-determined increment. If the high $SpO_2$ condition still exists at the next update time, the controller again sends a signal to decrease the $FiO_2$ flow rate by the pre-determined increment. The controller will continue to decrease the $FiO_2$ flow rate by the pre-determined increment until the high $SpO_2$ condition no longer exists or the $FiO_2$ flow rate is equal to the low end of the $FiO_2$ range.

The software algorithm also monitors the pulse oximeter output signal for a low $SpO_2$ condition. If the algorithm detects a low $SpO_2$ condition exists (i.e., the "step-up" decision point), the controller sends a signal to increase the $FiO_2$ flow rate by a pre-determined increment. If the low $SpO_2$ condition is detected after the next update time, the controller again sends a signal to increase the $FiO_2$ flow rate by the pre-determined increment. The controller will continue to increase the $FiO_2$ flow rate at each update time until the low $SpO_2$ condition no longer exists, or the $FiO_2$ flow rate is equal to the high end of the $FiO_2$ range.

If the low $SpO_2$ condition continues to exist and the pulse oximetry level has reached a low-low $SpO_2$ condition (i.e., the "alarm" decision point), the controller sends a signal to increase the $FiO_2$ flow rate to the maximum, preferably 100%, and an audible and/or visual alarm is actuated. The $FiO_2$ flow rate will be maintained at 100% by the controller until the alarm is acknowledged and cleared by the technician/operator. After the alarm has been cleared, the $FiO_2$ flow rate is reset to the mid-point of the $FiO_2$ range.

Figure 2:
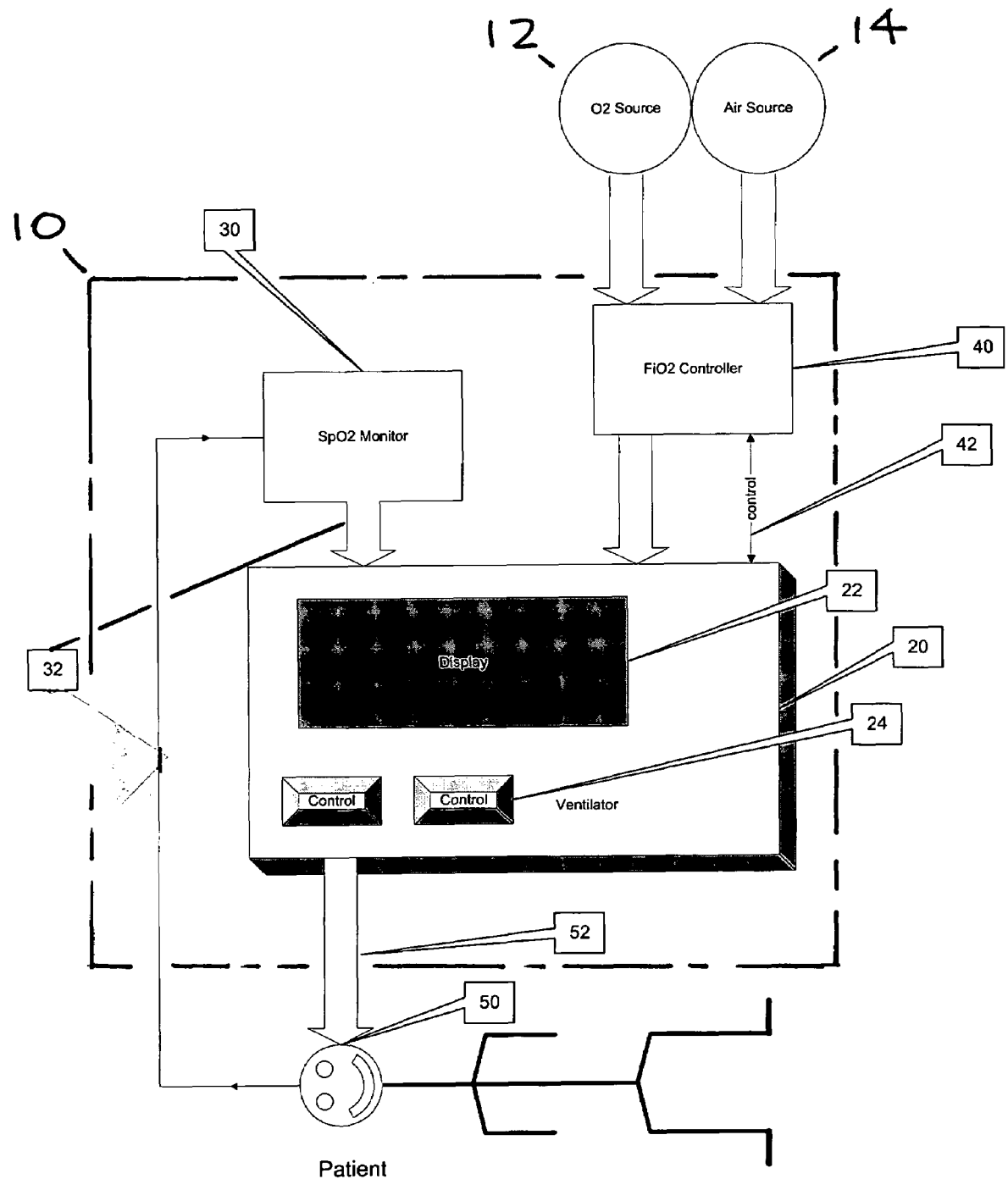
FIG. 2 is a block diagram of a ventilator system including the pulse oximeter and ventilator controller.

FIG. 2 shows a preferred ventilator system 10 wherein a pulse oximeter 30 measures the arterial oxygen saturation ($SpO_2$) of a patient and sends an output signal 32 to the ventilator controller 20. The ventilator controller 20 includes a display 22 and a keypad 24, which are used by a technician to enter pulse oximetry set point levels, the $FiO_2$ flow rate range, the values for the incremental changes in the $FiO_2$ flow rate (increased or decreased) when a pulse oximetry set point value is measured, the $SpO_2$ sample period for obtaining an average $SpO_2$ value and the update time. The $FiO_2$ flow rate controller 40 controls the mixture of oxygen 12 and air 14 which is provided to the patient. The ventilator controller 20 compares the average measured $SpO_2$ value to the set point levels entered by the technician and regulates the $FiO_2$ flow rate 52 to the patient by sending a signal 42 to the $FiO_2$ flow rate controller 40. Based on the signal from the ventilator controller 20, the $FiO_2$ flow rate controller 40 adds oxygen to the air. The $FiO_2$ flow rate controller 40 and the pulse oximeter 30 can be provided either integral with the ventilator controller 20 or external to it. In preferred embodiments, the $FiO_2$ flow rate controller 40 receives the signal 42 from the ventilator controller 20 and regulates the $FiO_2$ flow rate 52 to the patient interface device 50, typically a face mask or a nasal mask, or by tracheal intubation.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

I claim:

1. A method of operating a ventilator to control the fraction of pressure inspired oxygen ($FiO_2$), the method comprising:
    providing a pulse oximeter to measure a patient's pulse oximetry;
    providing a $FiO_2$ flow rate controller, wherein the flow rate controller controls the flow rate of $FiO_2$ to the patient;
    measuring the patient's pulse oximetry and providing a measured pulse oximetry value;
    averaging the patient's measured pulse oximetry value over a period of time;
    providing a ventilator controller responsive to the average of the patient's measured pulse oximetry value, wherein the $FiO_2$ flow rate controller is responsive to the ventilator controller and controls the flow rate of $FiO_2$ to the patient;
    selecting the time period for averaging the patient's measured pulse oximetry value;
    selecting a first, a second, and a third pulse oximetry level as set points for the ventilator controller;
    selecting an $FiO_2$ operating range having a low end, a high end and a mid-point, wherein the midpoint of the range is equal to one-half the sum of the low end and the high end;
    selecting a first incremental amount for decreasing the flow rate of $FiO_2$ and a second incremental amount for increasing the flow rate of $FiO_2$;
    selecting an update time interval, wherein the update time interval is the interval of time between comparisons by the ventilator controller of the set points and the averaged measured pulse oximetry value of the patient;

setting the FiO$_2$ flow rate controller at a flow rate equal to the mid-point of the operating range;

decreasing the flow rate of FiO$_2$ by the first incremental amount when the average pulse oximetry value is greater than the first level;

increasing the flow rate of FiO$_2$ by the second incremental amount when the average pulse oximetry value is less than the second level; and increasing the flow rate of FiO$_2$ to a maximum rate when the average pulse oximetry value is less than the third level.

2. The method of operating a ventilator according to claim 1, wherein the method further comprises maintaining the flow rate of FiO$_2$ at the maximum when the average pulse oximetry value is less than the third level and initiating an alarm condition.

3. The method of operating a ventilator according to claim 2, wherein the method further comprises manually resetting the alarm.

4. The method of operating a ventilator according to claim 3, wherein the period of time is about 10 seconds before the update time interval.

5. The method of operating a ventilator according to claim 1, wherein the period of time is from 5 to 60 seconds before the end of the update time interval.

6. The method of operating a ventilator according to claim 1, wherein the ventilator controller includes software which automatically adjusts the flow rate of FiO$_2$ based upon the average pulse oximetry value of the patient.

7. The method of operating a ventilator according to claim 1, wherein the update time interval is at least 30 seconds.

8. The method of operating a ventilator according to claim 1, wherein the ventilator controller includes a normal operating mode for the control of the flow rate of FiO$_2$.

9. The method of operating a ventilator according to claim 1, wherein the flow rate of FiO$_2$ does not change when the average pulse oximetry value is between the first level and the second level.

10. The method of operating a ventilator according to claim 1, wherein the alarm condition actuates an audible alarm signal, a visual alarm signal or both an audible alarm signal and a visual alarm signal.

11. The method of operating a ventilator according to claim 1, wherein the pulse oximetry is measured using a probe attached to the patient's finger, toe or ear lobe.

12. The method of operating a ventilator according to claim 1, wherein FiO$_2$ operating range is between about 40% and 100%.

13. The method of operating a ventilator according to claim 1, wherein FiO$_2$ operating range is between about 60% and 90%.

14. A method of operating a ventilator to control the fraction of pressure inspired oxygen (FiO$_2$), the method comprising:

providing a pulse oximeter to measure a patient's pulse oximetry;

providing a FiO$_2$ flow rate controller, wherein the flow rate controller controls the flow rate of FiO$_2$ to the patient;

measuring the patient's pulse oximetry and providing a measured pulse oximetry value;

averaging the patient's measured pulse oximetry value over a period of time;

providing a ventilator controller responsive to the average of the patient's measured pulse oximetry value, wherein the FiO$_2$ flow rate controller is responsive to the ventilator controller and controls the flow rate of FiO$_2$ to the patient;

selecting the time period for averaging the patient's measured pulse oximetry value;

selecting a first, a second, and a third pulse oximetry level as set points for the ventilator controller;

selecting an FiO$_2$ operating range having a low end, a high end and a mid-point, wherein the midpoint of the range is equal to one-half the sum of the low end and the high end;

selecting a first incremental amount for decreasing the flow rate of FiO$_2$ and a second incremental amount for increasing the flow rate of FiO$_2$;

selecting an update time interval, wherein the update time interval is the interval of time between comparisons by the ventilator controller of the set points and the averaged measured pulse oximetry value of the patient;

setting the FiO$_2$ flow rate controller at a flow rate equal to the mid-point of the operating range;

decreasing the flow rate of FiO$_2$ by the first incremental amount when the average pulse oximetry value is greater than the first level;

increasing the flow rate of FiO$_2$ by the second incremental amount when the average pulse oximetry value is less than the second level;

increasing the flow rate of FiO$_2$ to a maximum rate and initiating an alarm condition when the average pulse oximetry value is less than the third level;

maintaining the flow rate of FiO$_2$ at the maximum after an alarm condition is initiated; and resetting the alarm condition when the average pulse oximetry value increases above the third level.

15. The method of operating a ventilator according to claim 14, wherein the update time interval is at least 30 seconds.

16. The method of operating a ventilator according to claim 14, wherein the algorithm comprises a normal operating mode for the control of the flow rate of FiO$_2$.

17. The method of operating a ventilator according to claim 14, wherein the flow rate of FiO$_2$ does not change when the average pulse oximetry value is between the first level and the second level.

18. The method of operating a ventilator according to claim 14, wherein the update time is automatically set to less than 1 minute when the alarm condition is initiated.

19. The method of operating a ventilator according to claim 14, wherein the alarm condition actuates an audible alarm signal, a visual alarm signal or both an audible alarm signal and a visual alarm signal.

20. The method of operating a ventilator according to claim 14, wherein the pulse oximetry is measured using a probe attached to the patient's finger, toe or ear lobe.

21. A method of operating a ventilator to control the fraction of pressure inspired oxygen (FiO$_2$), the method comprising:

providing a pulse oximeter to measure a patient's pulse oximetry;

providing a FiO$_2$ flow rate controller, wherein the flow rate controller controls the flow rate of FiO$_2$ to the patient;

measuring the patient's pulse oximetry and providing a measured pulse oximetry value;

averaging the patient's measured pulse oximetry value over a period of time;

providing a ventilator controller responsive to the average of the patient's measured pulse oximetry value, wherein the FiO$_2$ flow rate controller is responsive to the ventilator controller and controls the flow rate of FiO$_2$ to the patient;

selecting a first, a second, and a third pulse oximetry level as set points for the ventilator controller, wherein the flow rate of $FiO_2$ does not change when the pulse oximetry is between the first level and the second level;

selecting an $FiO_2$ operating range having a low end, a high end and a mid-point, wherein the midpoint of the range is equal to one-half the sum of the low end and high end;

selecting a first incremental amount for decreasing the flow rate of $FiO_2$ and a second incremental amount for increasing the flow rate of $FiO_2$;

selecting an update time interval, wherein the update time interval is the interval of time between comparisons by the ventilator controller of the set points and the measured pulse oximetry of the patient and wherein the update time is at least 30 seconds;

setting the $FiO_2$ flow rate controller at a flow rate equal to the mid-point of the operating range;

decreasing the flow rate of $FiO_2$ by the first incremental amount when the average pulse oximetry value is greater than the first level and the flow rate is greater than or equal to the low end of the $FiO_2$ operating range;

increasing the flow rate of $FiO_2$ by the second incremental amount when the average pulse oximetry value is less than the second level and the flow rate is less than or equal to the high end of the $FiO_2$ operating range;

increasing the flow rate of $FiO_2$ to a maximum rate and initiating an alarm condition when the average pulse oximetry value is less than the third level, wherein the update time is automatically set to less than 1 minute when the alarm condition is initiated;

maintaining the flow rate of $FiO_2$ at the maximum after an alarm condition is initiated; and resetting the alarm condition when the average pulse oximetry value increases above the third level.

22. A ventilator system for controlling the fraction of pressure inspired oxygen ($FiO_2$) in air delivered to a patient, the ventilator system comprising:

a pulse oximeter which measures the pulse oximetry of a patient and generates an output signal in response thereto;

a ventilator controller comprising a keypad, a display and a software algorithm, wherein the keypad and display are adapted to enter an update time interval, a first, second, and third pulse oximetry level set points, a $FiO_2$ flow rate range, a first incremental amount for decreasing the flow rate of $FiO_2$ and a second incremental amount for increasing the flow rate of $FiO_2$; and a time period over which the patient's measured pulse oximetry value is averaged;

a $FiO_2$ flow rate controller responsive to the ventilator controller; and a face mask, nasal mask or endotracheal tube for delivering the air to the patient, wherein the ventilator controller software algorithm computes an average pulse oximetry value and, at the end of the update time interval, compares the average pulse oximetry value to the first, second and third pulse oximeter level set points, the ventilator controller automatically controlling the flow rate of $FiO_2$ to the patient such that the flow rate of $FiO_2$ decreases by a first incremental amount when the average pulse oximetry value is greater than the first level, increases the flow rate of $FiO_2$ by a second incremental amount when the average pulse oximetry value is less than the second level, and increases the flow rate of $FiO_2$ to a maximum rate when the average pulse oximetry value is less than the third level.

23. The ventilator system as set forth in claim 22, wherein the update time interval is the interval of time between comparisons by the ventilator controller software algorithm of the set points and the output signal of the pulse oximeter.

24. The ventilator system as set forth in claim 22, wherein the flow rate controller comprises a control valve.

* * * * *